United States Patent
Osterdahl et al.

(10) Patent No.: US 6,656,170 B2
(45) Date of Patent: *Dec. 2, 2003

(54) ABSORBENT ARTICLE WITH IMPROVED LEAKAGE SAFETY

(75) Inventors: Eje Osterdahl, Vastra Frolunda (SE); Asa Johansson, Gothenburg (SE); Ulrika Husmark, Molnlycke (SE); Ingrid Gustafson, Asa (SE); Anna Stoltze, Gothenburg (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/006,361

(22) Filed: Dec. 10, 2001

(65) Prior Publication Data

US 2002/0087133 A1 Jul. 4, 2002

Related U.S. Application Data

(60) Provisional application No. 60/251,875, filed on Dec. 8, 2000.

(30) Foreign Application Priority Data

Dec. 8, 2000 (SE) .............................................. 0004539

(51) Int. Cl.[7] .............................................. A61F 13/15
(52) U.S. Cl. .................................. 604/385.17; 604/379
(58) Field of Search ...................... 60/378, 379, 385.01, 60/385.17

(56) References Cited

U.S. PATENT DOCUMENTS

| | | | |
|---|---|---|---|
| 4,631,062 A | * 12/1986 | Lassen et al. | 604/385.02 |
| 4,673,403 A | * 6/1987 | Lassen et al. | 604/385.17 |
| 4,804,380 A | 2/1989 | Lassen et al. | |
| 5,382,245 A | * 1/1995 | Thompson et al. | 604/367 |
| 5,545,156 A | * 8/1996 | DiPalma et al. | 604/385.23 |
| 5,662,633 A | * 9/1997 | Doak et al. | 604/378 |
| 6,191,340 B1 | * 2/2001 | Carlucci et al. | 604/369 |
| 6,198,019 B1 | * 3/2001 | Hansson et al. | 604/378 |
| 6,392,117 B1 | * 5/2002 | Mayer et al. | 604/378 |
| 6,455,114 B1 | * 9/2002 | Goldhirsch et al. | 428/34.7 |
| 6,475,199 B1 | * 11/2002 | Gann et al. | 604/385.01 |
| 6,492,574 B1 | * 12/2002 | Chen et al. | 604/378 |
| 2002/0065497 A1 | * 5/2002 | Kolby-Falk | 604/368 |
| 2002/0082576 A1 | * 6/2002 | Hansson et al. | 604/381 |

FOREIGN PATENT DOCUMENTS

| | | | |
|---|---|---|---|
| EP | 0 768 072 | 4/1997 | |
| SE | WO 99/45099 | * 9/1999 | ............ C12N/1/20 |
| WO | WO 95/00095 | 1/1995 | |

* cited by examiner

Primary Examiner—Weilun Lo
Assistant Examiner—Michael G. Bogart
(74) Attorney, Agent, or Firm—Young & Thompson

(57) ABSTRACT

An absorbent article, such as a sanitary napkin, a panty liner, or a protector from female incontinence, is intended for wear in the crotch region of the wearer inside her underclothes. The article is generally elongate in shape and has two long sides, two short sides, two end-portions, a center portion disposed between the end-portions, a liquid-permeable casing sheet intended to lie proximal to the wearer's body in use, a liquid-impermeable casing sheet intended to lie distal from the wearer's body in use, and between the layers in a direction from the liquid-permeable casing sheet and towards the liquid-impermeable casing sheet a drainage layer, an absorption layer, and a hump-forming element which together with the drainage layer and the absorption layer forms a hump which projects out from the plane of the napkin on that side of the napkin which is intended to lie proximal to the wearer in use. At least one cut is made through the drainage layer and the absorption layer, and the hump-forming element is protruded up through the layers.

17 Claims, 3 Drawing Sheets

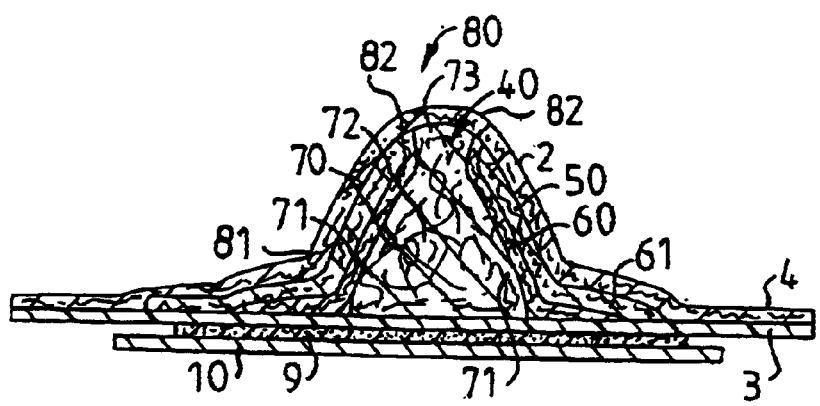
FIG.3
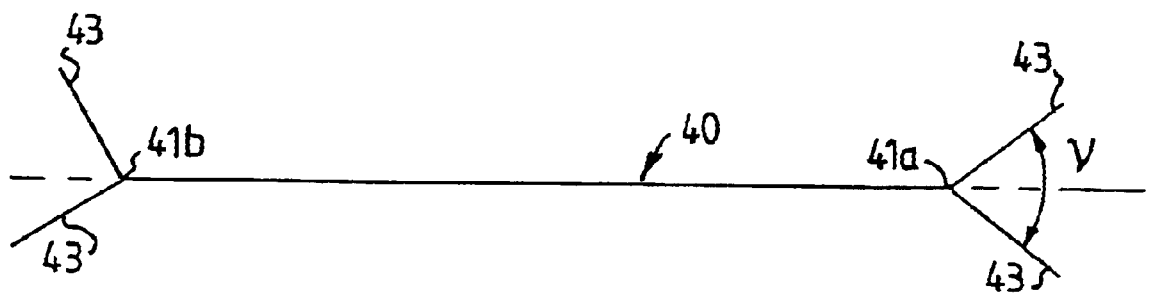
FIG.4
FIG.5

ABSORBENT ARTICLE WITH IMPROVED LEAKAGE SAFETY

This application claims the benefit of U.S. Provisional Application 60/251,875 filed on Dec. 8, 2000.

FIELD OF INVENTION

The present invention relates to an absorbent article, such as a sanitary napkin, a panty liner or an incontinence protector, which is intended to be carried in the crotch region of the wearer inside the wearer's panties or pants, said article having a generally elongated shape with two long sides, two short sides, two end-portions, a central portion located between the end-portions, a liquid-permeable casing sheet or top sheet which is intended to lie proximal to the wearer's body in use, a liquid-impermeable casing sheet or backing sheet intended to lie distal from the wearer's body in use, and between said sheets a drainage sheet and an element which forms a hump on the side of the article that lies proximal to the wearer's body in use, as seen in a direction from the liquid-permeable casing sheet towards the liquid-impermeable casing sheet.

BACKGROUND OF THE INVENTION

Conventional absorbent articles of the aforesaid kind are generally flat. Consequently, when the lower abdomen of the female carrier is not flat problems can occur when donning and wearing such articles. In such cases, abutment of the article with the wearer's body is not of the best and if gaps occur between product and the user's body there is a serious risk that body fluid will leak past the long side-edges of the article. Such leakage is particularly undesirable, since it is very liable to soil the wearer's clothes. Rearward leakage is a particular problem in this respect, which normally occurs when the user lies down, for instance at night.

With the intention of solving this problem, it has been proposed to provide the absorbent articles with a pre-formed hump. Absorbent articles that include humps are described in EP-A-0 419 434, among others. The intention of providing absorbent articles with pre-formed humps is to create contact with the genitals of the wearer in use. Discharged body fluids can be caught immediately on leaving the wearer's body and will be absorbed immediately by the article, without running out over its surface and over the long edges of the article.

Another drawback with flat articles is that when the article is used, it is influenced by forces exerted by the wearer's thighs for instance, so as to wrinkle the product and/or cause the long edges of the product to fold over the liquid-permeable surface thereof. A wrinkled surface and/or inwardly folded long edges of the product will significantly reduce the liquid-permeable surface and in many cases to a size that is insufficient to capture all liquid discharged by the wearer at one time, wherewith leakage may occur.

A conventional way of creating a hump is simply to provide a large amount of absorbent material in the absorbent pad within the area where the hump is desired, and form the hump from this excess material. Humps are most often formed from an absorbent material referred to as cellulose fluff pulp, in other words defibred pulp from, e.g., thermo-mechanical pulp, chemithermomechanical pulp, or chemical sulphite pulp or sulphate pulp. Such a material, however, is not stable when wet, and consequently a hump comprised of such material will collapse and lose its shape when wet. In order to obtain a hump consisting of cellulose fluff pulp and having sufficient height whilst the article is in use, it is necessary to use so much cellulose fluff pulp in the production of the hump as to cause the hump to be felt uncomfortable by the wearer. Another problem that occurs with an article constructed in accordance with the above DESCRIPTION is that control of the liquid dispersion capacity of the article in the z-direction is lost, because the article loses its shape when wetted. It is also known to produce an article which includes a hump that faces towards the wearer, by placing a moulding or shaping element on top of the absorbent core. One drawback in this respect is that the hump results in inertia in liquid transportation down into the product, due to the fact that the shaping element must be filled with liquid before it releases the liquid to the underlying absorption core, said core having a strong liquid suction and absorbing effect and also a liquid retaining absorption effect. A hump can also be provided on the upper side of the article, by providing a planar article with a shaping element that takes a convex shape in relation to the wearer when the sides of the article in the region of the crotch are subjected to greater loads from the wearer's thighs. The drawback with this solution is that the shaping element returns to its original planar state immediately the wearer does not subject the sides of the article to pressure, e.g. when she stands with her legs apart or sits in a "lotus position", and also because it is difficult to produce a shape that corresponds essentially to the body shape of the wearer, solely by flexural deformation.

An absorbent article of the kind described in the introduction is known from EP-A1-0 768 072. However, in this case, the hump-forming element also constitutes the element that shall absorb and store discharged liquid and comprises a compressible, resilient and wet-stable material.

An object of the present invention is to provide an absorbent article of the aforesaid kind that conforms well to the wearer's body, renders the risk of leakage but slight, and which allows a large volume of liquid discharged at one and the same time to be handled with only a slight risk of leakage.

SUMMARY OF THE INVENTION

These objects are achieved in accordance with the invention with an article of the kind described in the introduction that is characterised in that an absorption layer is disposed between the drainage layer and the hump-forming element, and in that the absorption layer and the drainage layer have a longitudinally extending cut along the longitudinal centre line of the article, where the underlying hump-forming element projects up through the absorption layer. Such a hump-forming element can be imparted highly effective liquid acquisition properties, meaning that a large volume of liquid delivered at one and the same time can be managed. The longitudinal cut in the absorption layer and the drainage layer also enables the material to be draped more easily around the hump-forming element, therewith enabling a pointed top on the hump to be obtained more readily.

In one preferred embodiment of the invention, at least that part of the hump-forming element that lies against the overlying absorption layer, i.e. the outer regions of the hump-forming material, is comprised of a material that has larger capillaries than the absorption layer and that preferably will present a somewhat retained shape in both a dry and a wet state, wherein that part of the hump-forming element that has been pushed up through the cut in the absorption layer and the drainage layer also has larger capillaries than the drainage layer. This results in an acquisition region that has an extra large capillary structure in the region of the cut up on the hump. A bordering absorption layer then drains the acquisition region and disperses the liquid within the absorption layer. This embodiment is particularly beneficial in those cases when a large volume of liquid is discharged over a short period of time.

The cut through the drainage layer and the absorption layer has a length of at least 20 mm, although preferably not greater than the length of the hump-forming element. In one beneficial variant, at least one of the end-portions of the longitudinally extending cut is joined to a further cut in the region of the end-portions of the longitudinally extending cut, these other angles defining between themselves and the imaginary extension of the longitudinal cut an angle γ of between 10°–90°, said other cut having a length of between 3–25 mm, preferably between 5–15 mm.

The hump-forming element is preferably comprised of a pressure yieldable, preferably resilient material, that may be an absorbent or a non-absorbent material.

In a further embodiment of the invention, the density of the hump-forming element increases successively away from the absorption layer in a direction towards the liquid-impermeable casing sheet.

The absorption layer will conveniently extend outwardly of at least a part of the contour line of the hump-forming element, but inwardly of the contour line of the drainage sheet. The absorption layer is placed on top of a drainage layer, because rapid acquisition of liquid into the hump is desired, which contributes to a drier and more comfortable surface proximal to the wearer, and provides a softer, more comfortable hump.

The absorption layer may consist of a dry-formed sheet that contains 5–100% cellulose fibre and which has a density of between 100–300 g/m$^3$, preferably between 200–250 g/m$^3$ and a weight by surface area of between 30–2000 g/m$^2$. The sheet will have been formed by compressing a web containing cellulose fibre in the absence of subsequent defibration and fluff forming, or by a compressed cellulose foam sheet that has a density of between 0.2–2.0 g/cm$^3$.

The hump preferably has an elongate form and narrows in a direction towards the end-portions of the article and, when seen from one short side of the article, preferably has a triangular cross-section that has a greater width at the base than at the top and preferably a length of between 20 mm and 140 mm and a height between 5–20 mm. The hump may be disposed generally in the centre part of the article or the rear end-portion of the hump may extend into the rear end-portion of the article. The forward end-portion of the hump will preferably not extend into the region of the front end-portion of the article. In the case of such an embodiment, the hump will lie against the wearer's crotch and will continue rearwards between the wearer's buttocks so as to contribute towards an effective seal, primarily when the wearer lies down, for instance to sleep.

BRIEF DESCRIPTION OF THE DRAWINGS

The invention will now be described in more detail with reference to the accompanying drawings, in which

FIG. 3 is a cross-sectional view of the sanitary napkin in FIG. 1, taken on the line III—III in said Figure;

FIGS. 4 and 5 illustrate examples of cuts in the drainage layer and the absorption layer;

DESCRIPTION OF EXEMPLIFYING EMBODIMENTS

Figure 1:
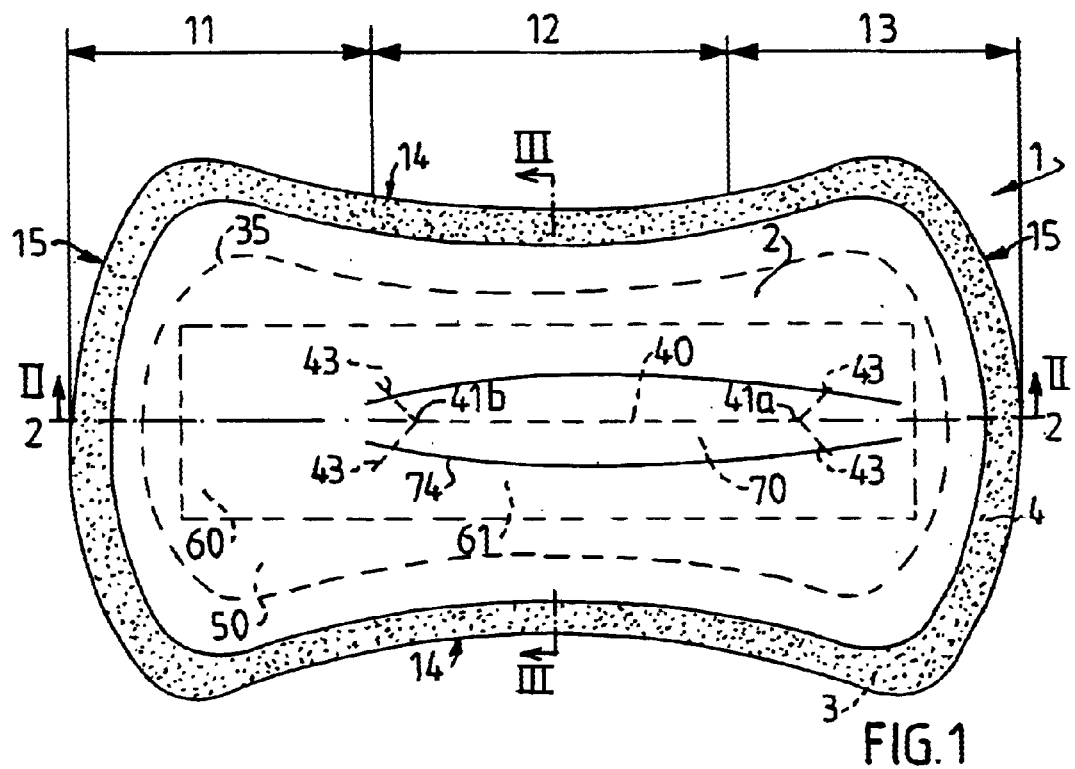
FIG. 1 is a plan view of a sanitary napkin according to a first embodiment of the invention, seen from the side that lies proximal to the wearer in use.

Although absorbent articles in the form of a sanitary napkin are described in the following exemplifying embodiments, it will be understood that these embodiments can also apply to a panty liner or female incontinence napkin. FIG. 1 illustrates a sanitary napkin 1 that has a generally elongate shape, with a longitudinal direction, a transversal direction, two long sides 14, two short sides 15, two end-portions 11, 13 and a central portion 12 located between said end-portions.

Figure 2:
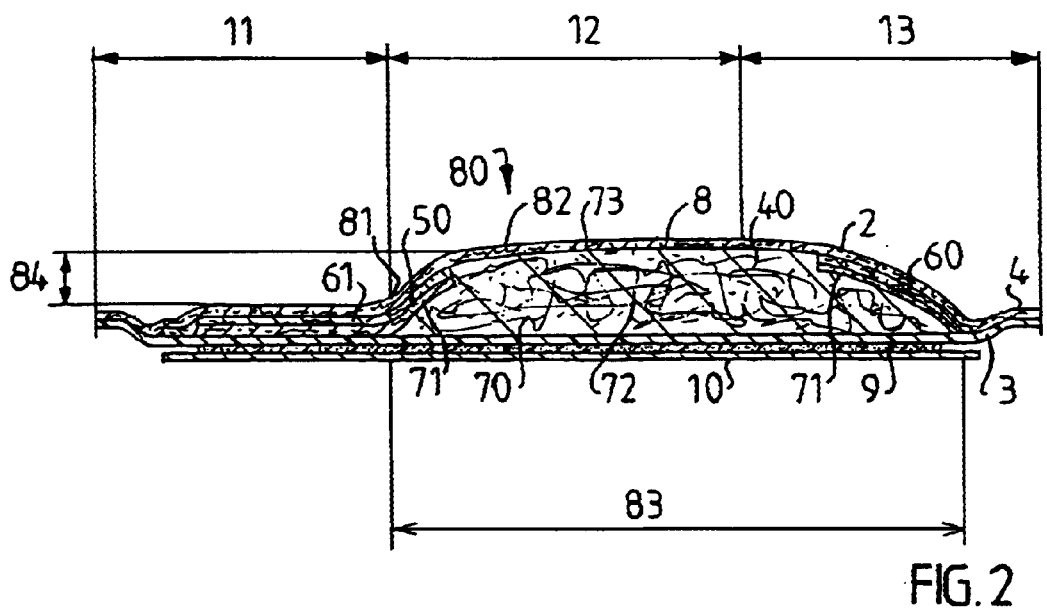
FIG. 2 is a longitudinally sectioned view of the sanitary napkin shown in FIG. 1, taken on the line II—II.

The sanitary napkin 1 shown in FIGS. 1, 2 and 3 includes a liquid-permeable casing sheet or top sheet 2 disposed on that side of the napkin 1 which is intended to lie proximal to the wearer in use. The liquid-permeable casing sheet 2 will conveniently consist in a somewhat soft, skin-friendly material. Different types of non-woven material are examples of suitable liquid-permeable materials. Other casing sheet materials that can be used are perforated plastic films, net, knitted, crocheted or woven textiles, and combinations and laminates of the aforesaid types of material.

The sanitary napkin 1 also includes a liquid-impermeable casing sheet or backing sheet 3, disposed on that side of the napkin 1 distal from the wearer in use. The liquid-impermeable casing sheet 3 is conventionally comprised of thin plastic film. Alternatively, there may be used a liquid-permeable material that has been rendered impermeable to liquid in some way or another. For instance, the liquid-permeable material may be coated with a glue that is impermeable to liquid, and the liquid-permeable layer laminated with a liquid-impermeable material, or hot-calendering a material that was initially liquid-permeable, such as to melt down the surface of the material and therewith obtain a liquid-impermeable layer. Alternatively, there may be used other textiles comprised of hydrophobic fibres and so impervious as to enable them to be used as a liquid barrier layer. The liquid-permeable casing sheet 3 may beneficially be vapour permeable.

The two casing sheets 2, 3 form a joining edge 4 that projects outwardly around the napkin contour line, and are mutually joined at this edge. The sheets may be joined together by means of any appropriate conventional technique, such as gluing, welding or sewing.

A drainage layer 50, absorption layer 60, and a hump-forming element 70 are disposed between the casing sheets 2, 3 as seen in a direction from the liquid-permeable casing sheet 2 towards the liquid-impermeable casing sheet 3. The absorption layer 60 extends beyond at least a part of a contour line 74 of the hump-forming element 70 but inwardly of a contour line 35 of the drainage layer 50.

The hump-forming element 70 forms together with the casing sheet 2, the drainage sheet 50 and the absorption layer 60 a central hump 80 that projects up from the plane of the napkin on that side of the napkin intended to lie proximal to the wearer in use. The central hump 80 is intended to lie against the wearer's body. The central hump 80 may have an elongate shape and may conveniently narrow or taper in a direction towards the end-portions 11, 13 of the napkin. The hump 80 has a generally triangular cross-section. In other words, when seen from one short side of the absorbent article, the hump has a greater width at the base 81 than at the top 82. The hump will preferably have a length 83 of between 20 mm and 140 mm, and a height 84 of between 5–20 mm.

The hump-forming element 70 is comprised at least partially of a pressure yieldable material, preferably a resilient material, although not necessarily an absorbent material. At least that part of the surface 71 of the hump-forming element that lies against the overlying absorption layer 60 has larger capillaries than the absorption layer or sheet 60. Because of the difference in capillary size between the absorbent layer 60 and the surface 71 of the hump-forming element 70 that lies against the absorption layer 60 (the absorption layer 60 has smaller capillaries than the material of the hump-forming element 70), there is no natural dispersion of liquid from the absorption layer 60 to the underlying hump-forming element 70 before the absorption layer reaches saturation.

The drainage layer 50 of the FIG. 1 embodiment is wider and longer than the absorption layer 60 and conveniently follows the outer contour of the periphery on the absorbent product inwardly of the joining region 4 between the two casing sheets 2, 3. This creates an absorption acquisition area 61 around the hump base 81 as a safety zone in the event that there is insufficient time for liquid to be absorbed at the top 82 of the hump 80. This non-absorbed liquid would then run down towards the base 81 of the hump 80 and there be absorbed in the safety area 61.

Material suited for the drainage layer 50 is dry-defibred cellulose admixed with an adhesive type binder, or bonding fibres, tissue material, or non-woven material having a capillary size that is in accord with the above reasoning.

The absorption layer 60 placed beneath the drainage layer 50 and draped over the hump-forming element 70 shall constitute the layer capable of receiving and storing essentially all liquid discharged by the wearer. The absorption layer has smaller capillaries than the overlying drainage layer 50. The absorption layer 60 may, for instance, be produced from cellulose pulp. This pulp may exist in rolls, bales or sheets that are dry-defibred and converted in a fluffed state to a pulp mat, sometimes with an admixture of superabsorbents, which are polymers capable of absorbing several times their own weight of water or body liquid (fluid). Examples of other usable materials are different types of foamed materials known, for instance, from SE 9903070-2, natural fibres, such as cotton fibres, peat, or the like. It is, of course, also possible to use absorbent synthetic fibres, or mixtures of natural fibres and synthetic fibres. Patent Application SE 9903070-2 describes a compressed foam material of regenerated cellulose, e.g. viscose. Such foam material will preferably have a density of 0.1 to 2.0 g/cm$^3$.

The absorbent material may also contain other components, such as foam-stabilising means, liquid-dispersing means, or a binder, such as thermoplastic fibres, for instance, which have been heat-treated to hold short fibres and particles together so as to form a coherent unit. A suitable material for the absorbent layer 60 according to the invention is the absorbent material described in WO 94/10956. This material is a dry-formed fibre layer of high density and stiffness that can follow the shape of hump element. In this case, the density will preferably be between 100–300 g/m$^3$ and preferably between 200–250 g/m$^3$. This material can be used directly in an absorbent article, without being first defibred. WO 94/10953 describes another, similar material that has particularly suitable properties for blood absorption purposes.

A fastener means 9 in the form of an elongate rectangular region of self-adhesive is provided on the surface of the liquid-impermeable casing sheet 3 that lies distal from the wearer in use. The fastener means 9 extends over the major part of the liquid-impermeable casing sheet 3. The invention is not restricted to the extension of the fastener means 9, and said means may have the form of elongate stripes, transverse regions, dots, circles, or other patterns and configurations. Neither is the invention restricted to the use of solely adhesive fastener means, since friction fasteners may be used and other types of mechanical fasteners, such as press studs, clips, girdles, pants or the like may be used when found suitable to do so.

When a pressure-sensitive adhesive is used to fasten the sanitary napkin in the panties of the wearer, it is usual to cover the adhesive with a removable protective layer 10 which has release properties on at least that side which faces towards the adhesive medium, so as to protect the adhesive against dirt and also to prevent the adhesive from adhering to other, undesired surfaces or against itself until the napkin shall be used.

In the case of the illustrated embodiment, the hump-forming element 70 extends over large parts of the rear end-portion 13 of the sanitary napkin, which provides a corresponding longitudinally extending hump 80 that projects out from the plane of the napkin on that side thereof intended to lie proximal to the wearer in use. It is particularly beneficial that the end-part 11 placed over the mons veneris is free from the hump 80, since the napkin will then conform better to the curvature of the wearer's body. The napkin 1 is intended to be turned towards the wearer so that the hump will lie against the crotch region of the wearer and so that the hump continues rearwardly between the wearer's buttocks and therewith contribute towards an effective seal, primarily when the wearer lies down, for instance to sleep.

Alternatively, the hump 80 may be allowed to extend essentially over a central part of the napkin.

The absorbent layer 60 and the drainage layer 50 have a cut 40 that extends longitudinally along the centre line A—A on the napkin and through which underlying material in the hump-forming element 70 has been pushed through the two material layers, the drainage layer 50 and the absorption layer 60. The length of the cut 40 may be at least 20 mm, preferably not greater than the length of the hump-forming element 70. That part 73 of the hump-forming element that has been pushed up through the cut 40 will beneficially have larger capillaries than the drainage layer. This results in an acquisition surface that presents large liquid-receiving space which enables liquid to quickly enter the napkin, which is to advantage, particularly in those instances when large volumes of liquid are discharged over a short space of time. It is beneficial when that part 73 of the hump-forming element that is pushed up through the absorbent layer 60 and the drainage layer 50 includes a material which will not bind liquid strongly to its fibres but lead the liquid further to the absorption layer 60, so that no liquid will remain close to the liquid-permeable casing sheet 2, such liquid otherwise contributing towards a wet surface against the user's skin. Fibres that can be considered suitable in the part 73 of the hump-forming element 70 are non-absorbent synthetic fibres, absorbent fibres that have been treated to render them hydrophobic and are therewith no longer absorbent.

The provision of a longitudinally extending cut 40 in the drainage layer 50 and the absorption layer 60 enables the triangular profile on the hump 80 to be maintained more easily, even when the hump is subjected to load from the user's body.

FIGS. 4 and 5 show examples of cut configurations. The length of the cut 40 is suitably at least 20 mm, although preferably not longer than the length of the hump-forming element 70. The cut 40 may consist solely of a simple longitudinal cut such as that shown in FIG. 4, or a cut such as that described in FIG. 5. It has been found beneficial to join the end-portions 41a, 41b of the longitudinal cut (see FIG. 5) to further cuts 43 that form an angle γ between themselves and the imaginary extension of the longitudinal cut 40, said angle being between 10°–90°. This enables the cut 40 to be opened more easily, so as to enable hump-forming material 70 to be pushed up through both layers, i.e. the drainage layer 50 and the absorption layer 60. The length of the cuts 43 is between 3–25 mm, preferably between 5–15 mm. It is not necessary for the cuts 43 on respective sides on the longitudinal cut 40 to have the same lengths or placements in relation to the longitudinal cut 40, neither is it necessary for the cuts 43 to be made in the same way at the two end-portions 41a, 41b.

In the case of the preferred embodiment, the cut 40 is made without removing material from the drainage layer 50 and the absorption layer 60, which is preferred. It is, of course, feasible to form the cut by providing a cut-out in the layers 50, 60, although this method is not preferred as it complicates manufacture.

Figure 6:
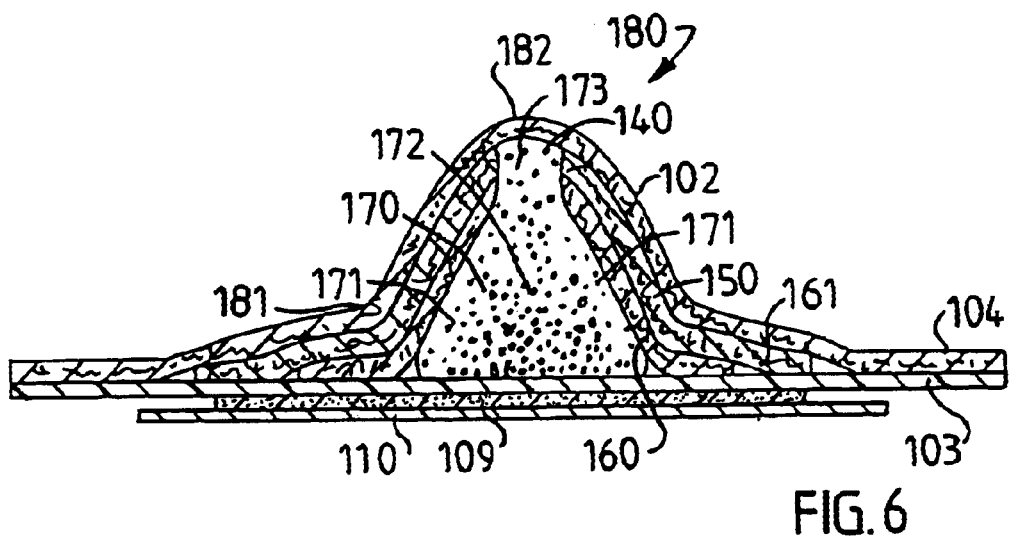
FIG. 6 is a cross-sectional view similar to FIG. 3 and shows another variant of a hump according to the second embodiment of the invention.

FIG. 6 is a view similar to the view of FIG. 3 and illustrates a second embodiment of a hump 180, where the density of the hump-forming element 170 increases successively down away from the absorbent layer 160 and towards the liquid-impermeable casing sheet 103. In other respects, the components of the FIG. 6 embodiment are the same as corresponding components in the embodiment according to FIGS. 1–3. Consequently, the components of the FIG. 6 embodiment have been given the same reference signs as corresponding components in FIGS. 1–3, to which 100 has been added. The sparsely drawn dots ins FIG. 6 are intended to illustrate low density and therewith large capillary sizes, while the tightly packed dots are intended to show successively higher density and therewith successively smaller capillaries. In this way, there is obtained an acquisition area that has an extra large pore structure in the region of the cut 140 up on the top 180 of the hump, wherewith some of the liquid can be drained out and dispersed further by the adjacent absorption layer 160, at the same time as some of the liquid is dispersed and stored within the hump-forming element 170. The description earlier given with reference to FIGS. 1–3 also applies to the hump 180 in FIG. 6, in other words it is beneficial for that part 173 of the hump-forming element that projects up through the absorption layer 160 and the drainage layer 150 to include a material that will not bind the liquid to the fibres of said material too firmly, but that will lead the liquid to the absorption layer 160, so that no liquid that might otherwise contribute to a wet surface against the wearer's skin will remain close to the liquid-permeable casing sheet. It is desirable that at least the central part 172 of the hump-forming element is shape-stable in both a dry and a wet state.

The hump-forming element according to the afore-described embodiments may consist of an absorbent structure, cellulose pulp consisting of absorbent or non-absorbent, natural or synthetic fibres, foamed material or material or mixtures thereof. Fibres that can be used to advantage are cellulose fibres of CTMP or CP quality, cotton, rayon, PP fibres, PE fibres and synthetic fibres whose surfaces have been made hydrophilic. The above-described structures, fibres and mixtures thereof may also contain particles of a superabsorbent material that is either distributed uniformly in said material or disposed in layers. By superabsorbent material is meant polymers that exist in the form of fibres, flakes, particles, granules, or the like, and which are capable of absorbing several times their own weight of body liquid whilst swelling and forming a gel. In order to obtain different densities in hump-forming elements 160, the element may be given the form of a mat, i.e. by delivering a flow of relevant fibre material and air to a mould the includes evacuation holes in a number of stages, and thereafter evacuating the air and compressing therebetween parts of the formed hump-forming element 170 to a desired density. Alternatively, layers of mutually different densities may be combined.

Figure 7:
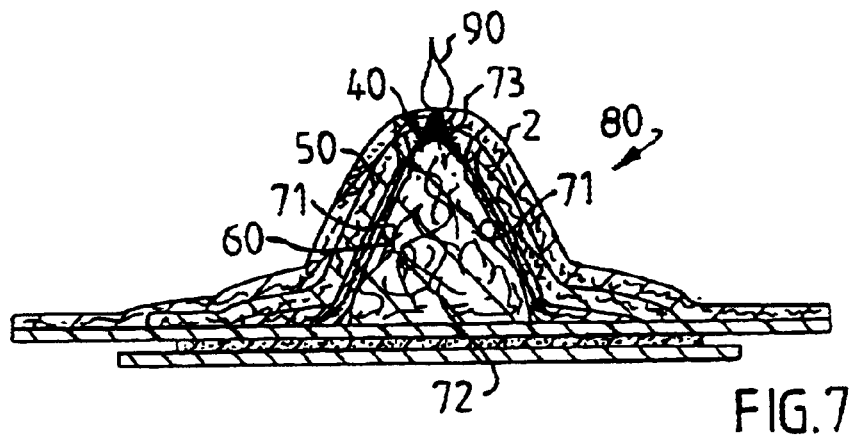
FIG. 7 is a cross-sectional view similar to that of FIG. 3 in which liquid dispersion in the hump is drawn schematically.
Figure 8:
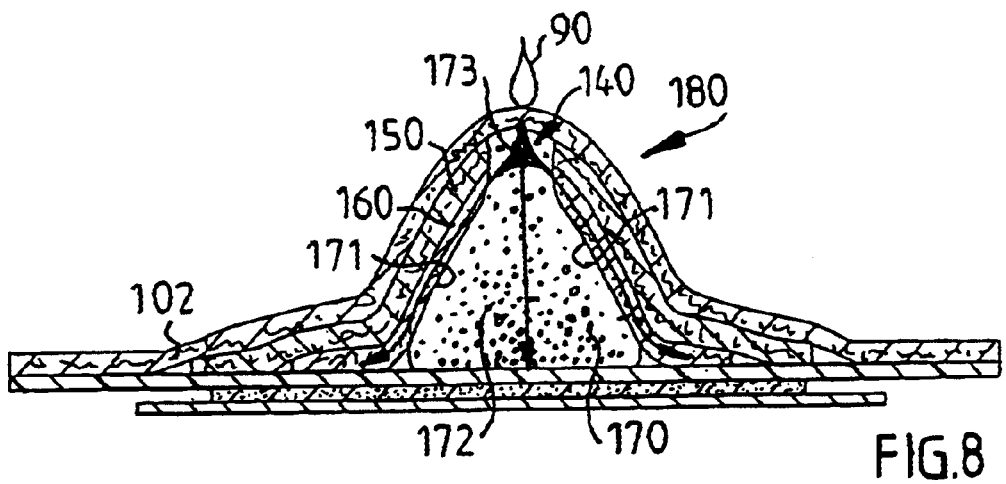
FIG. 8 is a cross-sectional view similar to that of FIG. 6, where liquid dispersion in the hump is drawn schematically.

FIGS. 7 and 8 illustrate schematically dispersion of the liquid essentially down into the napkin, the extent of this dispersion being dependent on the variant of hump-forming element chosen for use in the various embodiments.

FIG. 8 illustrates a hump that is provided with a cut 140 through the drainage layer 150 and the absorption layer 160. The element surface 171 that lies against the absorption layer 160 and that part 173 of said element 170 that projects up through the drainage layer 150 and the absorption layer 160 shall at least have a capillary size that is greater than the capillary size of the absorption layer. The capillary size of the central part 172 of said element decreases gradually in a direction towards the liquid-impermeable casing sheet 103, so as to form a natural absorption gradient down in the central part 172 of the hump-forming element. Liquid 90 is absorbed in z-directions through the casing sheet 102 and down into that part 173 of the hump-forming element 170 that has been pushed up through the cut 140, and from there down to the underlying absorption layer 160 where some of the liquid is dispersed further in said layer 160 and stored therein. As a result of the capillary size gradient, some of the liquid may disperse downwards in the central part 172 of the hump-forming element.

Due to its three-dimensional form adapted to fit the woman body, the article according to the invention is very suitable for carrying an active substance. Examples of suitable active substances are given in WO-A1-99/17813, which is referred to for further details. In WO-A1-99/45099 the use of *Lactobacillus plantarum*, strain LB931, which has been deposited at Deutsche Sammlung von Mikroorganismen, and been assigned accession number DSM11918, in absorbent articles is disclosed. Preferably, LB931 is comprised in the article according to the invention in the area thereof coming in contact with the urogenital region, i.e. perineum, urethra and vagina. The active substance is thus disposed on the area of the article comprising the hump-forming element. The active substance is preferably disposed on the liquid-permeable casing sheet or on the drainage sheet and also on the part of the hump-forming element that projects through the absorbent layer and the drainage layer.

It will be understood that the invention is not restricted to the described and illustrated exemplifying embodiments thereof and that further variants and modifications are conceivable within the scope of the accompanying claims. All conceivable combinations of the described embodiments are intended to be included by the invention.

A List of Numeric References Made in the FIGS.
1=Sanitary napkin
2,102=Liquid-permeable casing sheet
3,103=Liquid-impermeable casing sheet
4,104=Joined between the two casing sheets
9,109=Fastener means
10,110=Protective layer with release properties for the fastener means 11,111=The forward end-portion of the napkin
12,112=The centre portion of the napkin
13,113=The rear end-portion of the napkin
14,114=The long sides of the napkin
15,115=The short sides of the napkin
40,140=A longitudinally extending cut
41a=One end-part region of the longitudinally extending cut
41b=Another end-part region of the longitudinally extending cut
43=Cuts at angles to the longitudinally extending cut
50,150=Drainage layer
35=Drainage layer contour line
60,160=Absorption layer
61,161=Absorption receiving range around the base of the hump
70,170=Hump-forming element
71,171=Periphery of the hump-forming element
72,172=Central part of the hump-forming element
73,173=That part of the hump-forming element that is pushed through the cut
74,174=The contour line of the hump-forming element
80,180=A sanitary napkin hump
81,181=Hump base
82,182=Top of the hump
85,185=End-portions of the hump
84,184=Hump height
83,183=Hump length
90) Liquid.

What is claimed is:

1. An absorbent article intended to be carried in the crotch region of a wearer inside the wearer's underclothes, wherein the article has a generally elongate form and comprising:

two long sides;

two short sides;

two end-portions;

a central part between said end-portions;

liquid-permeable casing sheet intended to be turned towards the wearer's body;

a liquid-impermeable casing sheet intended to be turned away from the wearer's body;

a drainage layer and a hump-forming element that provides a preformed hump on that side of the article which is proximal to the wearer's body in use between said sheets in a direction from the liquid-permeable casing sheet towards the liquid-impermeable casing sheet;

an absorption layer disposed between the drainage layer and the hump-forming element; and a cut in the absorption layer and the drainage layer, the cut extending along the longitudinal center line of the article and via which a part of the underlaying hump-forming element is projected through the absorption layer and the drainage layer.

2. The absorbent article according to claim 1, wherein at least the part of the hump-forming element that lies against the overlying absorption layer is comprised of a material that has larger capillaries than the absorption layer; and wherein the part of the hump-forming element that projects up through the absorption layer and the drainage layer has larger capillaries than the drainage layer.

3. The absorbent article according to claim 1, wherein the cut has a length of at least 20 mm.

4. The absorbent article according to claim 1, wherein at least one of the end-portions of the longitudinally extending cut is joined to a further cut in the region of the end-portions of said longitudinally extending cut, wherein said further cut defines between itself and the imaginary extension of the longitudinal cut an angle of between 10–90°; and in that said further cut has a length of between 3–25 mm.

5. The absorbent article according to claim 1, wherein the hump-forming element is comprised of a pressure yieldable material.

6. The absorbent article according to claim 1, wherein the hump-forming element is comprised of a non-absorbent material.

7. The absorbent article according to claim 1, wherein the hump-forming element is comprised of an absorbent material.

8. The absorbent article according to claim 1, wherein the density of the hump-forming element increases successively in a direction away from the absorption layer and towards the liquid-impermeable casing sheet.

9. The absorbent article according to claim 1, wherein the absorption layer extends outwardly of at least a part of a contour line of the hump-forming element, but inwardly of a contour line of the drainage layer.

10. The absorbent article according to claim 1, wherein the absorption layer is comprised of a dry-formed sheet containing 5–100% cellulose fiber and having a density of between 100–300 $g/m^3$ and a weight per unit area of between 30–2000 $g/m^2$, said sheet having been formed by compressing a web containing cellulose fibers in the absence of subsequent defibration and fluff formation.

11. The absorbent article according to claim 1, wherein the absorption layer is comprised of a compressed sheet of cellulose foam having a density of between 0.2–2.0 $g/cm^3$.

12. The absorbent article according to claim 1, wherein the hump has an elongate shape and narrows towards the end-portions of said article and, when seen from one short side of the article, said hump presents a triangular cross-section that has a greater width at the base than at the top and a length of between 20 mm and 140 mm and a height of between 5–20 mm.

13. The absorbent article according to claim 12, wherein the hump is disposed generally in the central part of the article.

14. The absorbent article according to claim 1, wherein the rear end-part of the hump extends into the rear end-portion of said article.

15. The absorbent article according to claim 14, wherein the forward end-portion of the hump terminates short of the region of the forward end-portion of said article.

16. The absorbent article according to claim 1, wherein an active substance is disposed on the liquid-permeable casing sheet or the drainage layer in the area thereof comprising the hump-forming element and on the part of the hump-forming element that projects up through the absorption layer and the drainage layer.

17. The absorbent article according to claim 16, wherein the active substance is *Lactobacillus plantarum, strain LB*931, which has been deposited at Deutsche Sammlung von Mikroorganismen, and has been assigned accession number DSM11918.

* * * * *